United States Patent [19]

Kurimoto et al.

[11] Patent Number: 5,362,490
[45] Date of Patent: Nov. 8, 1994

[54] HUMAN MYELOMONOCYTE INTERFERON-GAMMA, AND PROCESS FOR PREPARATION AND USE THEREOF

[75] Inventors: Masashi Kurimoto; Masakazu Mitsuhashi, both of Okayama, Japan

[73] Assignee: Kabushiki Kaisha Hayashibara Seibutsu Kagaku Kenkyujo, Okayama, Japan

[21] Appl. No.: 62,323

[22] Filed: May 17, 1993

Related U.S. Application Data

[63] Continuation of Ser. No. 658,740, Feb. 22, 1991, abandoned, which is a continuation-in-part of Ser. No. 78,005, Jul. 21, 1987, abandoned, and a continuation-in-part of Ser. No. 379,318 Jul. 13, 1989, abandoned.

[30] Foreign Application Priority Data

Jul. 25, 1986 [JP] Japan ................. 61-176266
May 25, 1987 [JP] Japan ................. 62-125777
Jul. 25, 1988 [JP] Japan ................. 63-184069

[51] Int. Cl.$^5$ .............. A61K 37/66; C12P 21/02; C07K 7/00
[52] U.S. Cl. .................. 424/85.5; 435/70.5; 530/351; 530/413; 424/85.1; 424/85.2; 424/85.6; 424/85.7
[58] Field of Search ............ 530/351; 435/70.5; 424/85.4; 514/2

[56] References Cited

U.S. PATENT DOCUMENTS 4,791,101 12/1988 Adolf ....................... 514/2
4,946,674 8/1990 von Eichborn et al. ........ 424/85.5

FOREIGN PATENT DOCUMENTS 3423234 2/1986 Germany.
60-64999 4/1985 Japan.

OTHER PUBLICATIONS

Yamamoto et al., Studies on the Sugar Chains of Interferon from Human Peripheral-Blood Lymphocytes, *J. Biochem.* 105:1034–1039 (1989).
Miyata et al. (1986) J. Biochem. 99 1681–1688.
Braude (1984) Biochemistry 23 5603–5609.
Gray et al. (1982) Nature 295:503–508.
Devos et al (1984 J. Interferon Res. 4 461–468.

*Primary Examiner*—Robert A. Wax
*Assistant Examiner*—Gabriele E. Bugaisky
*Attorney, Agent, or Firm*—Browdy and Neimark

[57] ABSTRACT

The present invention relates to a novel human interferon-gamma derived from an established human myelomonocyte, a process to prepare said interferon-gamma, and its use. The human myelomonocyte interferon-gamma has a novel polypeptide and carbohydrate chain structure, and it is effective in preventing and treating viral diseases, malignant tumors and immunopathies alone or in combination with other lymphokine and/or chemotherapeutic.

22 Claims, 2 Drawing Sheets

HUMAN MYELOMONOCYTE INTERFERON-GAMMA, AND PROCESS FOR PREPARATION AND USE THEREOF

CROSS REFERENCE TO RELATED APPLICATIONS

This application is a continuation, of application Ser. No. 07/658,740 filed Feb. 22, 1991 now abandoned, which is a continuation-in-part of Ser. No. 07/078,005, filed Jul. 21, 1987 now abandoned, and a continuation-in-part of Ser. No. 07/379,318, filed Jul. 13, 1989 now abandoned, both of which applications are incorporated hereby by reference in the entirety.

BACKGROUND OF THE INVENTION

1. Field of the Invention

The present invention relates to a novel human myelomonocyte interferon-gamma, a process for preparing this interferon-gamma, and its use.

More particularly, the present invention relates to a novel human myelomonocyte interferon-gamma, and a process for preparing this interferon-gamma, characterized by allowing an established human myelomonocyte capable of producing myelomonocyte interferon-gamma to produce the interferon-gamma, and recovering the accumulation; a process for preparing a monoclonal anti-interferon-gamma antibody using the myelomonocyte; and a method for purifying the interferon-gamma using the monoclonal antibody, as well as to a prophylactic and therapeutic agent for interferon-gamma susceptible disease, these agents containing the human myelomonocyte interferon-gamma as an effective ingredient thereof.

2. Description of the Prior Art

As described in Sigeyasy Kobayashi, "Interferon", published by Kodansha Co., Ltd. Tokyo, Japan (1975), D. A. J. Tyrrell, "Interferon and its Clinical Potential", published by William Heinemann Medical Books Ltd., London (1976), and *Protein, Nucleic Acid and Enzyme*, Vol. 21, No. 4, pp. 245-333 (1976), interferon is a name used to designate glycoproteins that can be extracellularly induced in a viable cell by subjecting the cell to the action of an interferon inducer, such as a virus, a bacterium, a protozoon, rickettsia, nucleic acid endotoxin, or polysaccharide. These glycoproteins also are capable of nonspecifically inhibiting viral growth.

This activity has made interferons potential prophylactic and therapeutic agents for viral diseases. Recent studies revealed that interferons exert an antioncotic activity on viral tumors, as well as on nonviral tumors. Because of the activity of interferons, there is much interest in developing pharmaceuticals using interferons.

Interferons include interferon-alpha (or leukocyte interferon), interferon-beta (or fibroblast interferon), and interferon-gamma (or immune interferon). Preparation of interferon-alpha and interferon-beta has been effected by using leukocytes and fibroblast cells. Recently, pharmaceuticals containing these interferons have been commercialized.

The interferons hereinafter will be abbreviated as "IFN-alpha", IFN-beta", and "IFN-gamma", occasionally with the prefix "Hu" indicating human origin.

Although various methods have been proposed for preparing HuIFN-gamma, no method has as yet been practiced on an industrial scale.

The methods using leukocytes or T lymphocytes derived from human peripheral blood, as disclosed, for example, in Japanese Patent Laid-Open Publications Nos. 58,891/82, 82,092/94, 70,099/85, 87,300/85, 129,700/85 and 149,600/85, International Patent Publication in Japanese Nos. 500,961/82 and 502,032/83, are not commercially useful because it is difficult to obtain an ample supply of the starting cells and these cells do not produce sufficient HuIFN to be commercially useful.

Japanese Patent Laid-Open No. 98,118/80 discloses a method wherein a human cell, which is obtained by implanting an established human cell into a non-human warm-blooded animal, or placing the cell into a diffusion chamber provided inside or outside of the body of a non-human warm-blooded animal, and allowing the cell to proliferate while allowing the cell to receive the nutrient body fluid from the animal, is used for preparing HuIFN-gamma. This method is characterized by an ample supply of the cell which is the starting material.

We found that the HuIFN-gamma productivity of the method varies with the type of the human cell used. Thus, the method can be improved to prepare consistently high-titered HuIFN-gamma so as to be practical for use on an industrial scale.

It is known that HuIFN-gamma is much stronger in cytostatic and antioncotic activities as compared with HuIFN-alpha or HuIFN-beta. Also, it is known that the combination of HuIFN-gamma with HuIFN-alpha and/or HuIFN-beta augments the antiviral, cytostatic and antioncotic activities of HuIFN-gamma. For these reasons, development of an industrial-scale preparation of HuIFN-gamma has been in great demand.

SUMMARY OF THE INVENTION

In view of the foregoing, we screened various established human cells, specifically, established human lymphoblastoid cells, for their ability to produce HuIFN-gamma on an industrial scale, as well as the potential for using HuIFN-gamma so produced as prophylactic and therapeutic agents for HuIFN-gamma susceptible diseases.

As a result, we unexpectedly discovered that established human myelomonocytes produce much greater quantities of HuIFN-gamma than other lymphoblastoid cells, and are suitable for use as HuIFN-gamma producer cells. The HuIFN-gamma obtained by the process of the present invention is a novel unique HuIFN-gamma because its polypeptide and carbohydrate chains differ from those of conventionally produced HuIFN-gamma. Moreover, human IFN-gamma obtained from human myelomonocyte has a superior efficacy when used for prevention and treatment of HuIFN-gamma susceptible diseases.

DETAILED DESCRIPTION OF THE INVENTION

Figure 1:
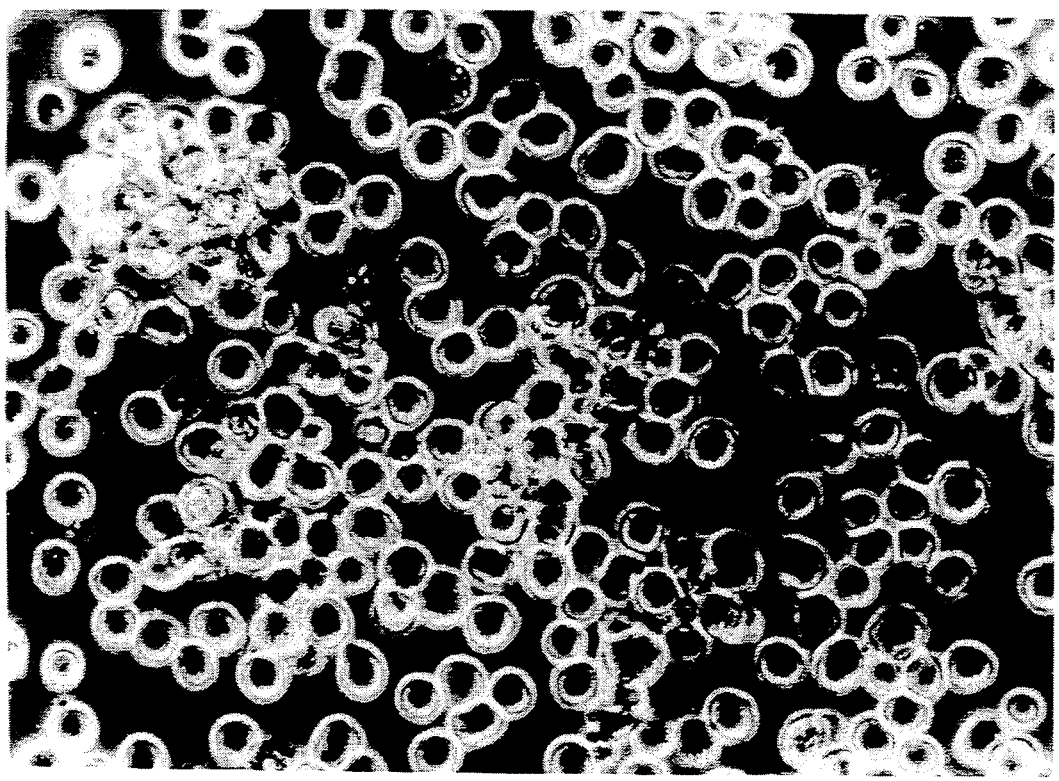
FIG. 1 is the phase-contrast microscopic view of HBL-38 cells.

The term "Established human myelomonocyte" means those cells which are not T or B cells and which can be identified by detecting the presence of myelomonocytic antigen by antigen-antibody reaction; for example, those as described in *Iwanami Koze Men-*

*eki Kagaku* (*The Iwanami Immunology Series*), Vol. 3, "Immunity Responsive Cells," edited by Tadamitsu Kishimoto and Takeshi Watanabe, pp. 181–204, published by Iwanamishoten Publisher, Tokyo, Japan (1986), and "Mammalian Cell Culture Technology," written by Mikio Shikita and Isao Yamane, pp. 141–162, published by Soft Science Publications, Tokyo, Japan (1985).

Examples of such myelomonocytes include HBL-38 cells established by the present inventors; HL-60 cells (ATCC CCL 240), KG-1 cells (ATCC CCL 246), ML-1 cells, ML-2 cells, ML-3 cells, THP-1 cells (ATCC TIB 202) and U-937 cells (ATCC CRL 1593) as described in the above-cited references; and CTV cells as reported in *Japanese Journal of Cancer Research* (*Gann*), Vol. 75, pp. 660–664 (1984). The HBL-38 cells are particularly useful in practicing the present invention because this cell type produces a greater amount of human myelomonocyte IFN-gamma. In order to augment the proliferation rate and the amount of human myelomonocyte IFN-gamma, the gene coding for human myelomonocyte IFN-gamma production can be introduced into a readily subculturable established human cell by cell fusion using, for example, polyethylene glycol or Sendai virus, or by recombinant gene techniques using DNA ligase, restriction enzyme (nuclease) and DNA polymerase. If necessary, the human myelomonocyte IFN-gamma can be advantageously prepared by using a method in which a human myelomonocyte IFN-gamma polypeptide chain, which is prepared by a recombinant microorganism such as recombinant *E. coli*, or by organic and chemical synthesis, or biochemical synthesis, is subjected, for example, to the action of a glycosyl transferase to transfer a carbohydrate chain to the polypeptide chain in a biochemical manner.

The method of proliferation for the human myelomonocyte can be suitable selected. Examples of such methods include tissue culture wherein human myelomonocyte is inoculated on a nutrient culture medium and cultured in vitro; and the method wherein human myelomonocytes is implanted into a non-human warm-blooded animal or in a diffusion chamber placed inside of or outside of the body of a non-human warm-blooded animal, and then allowed to proliferate while receiving the nutrient body fluid from the animal.

The in vitro proliferation will be explained first.

In the in vitro proliferation, any nutrient culture medium can be used, as long the human myelomonocyte proliferates therein. Examples of these are RPMI 1640 medium and Eagle's minimal essential medium. These culture media may be modified by supplementation with vitamin, mineral, carbohydrate, amino acid and/or mammalian serum.

The culture may be a monolayer or a suspension culture. The temperature is about 20°–40° C., preferably about 35°–38° C., and the inoculum should have a cell number per ml culture medium that attains a maximum proliferation over a period of about one week, preferably about $10^4$–$10^7$ cells/ml culture medium.

The culture medium containing human myelomonocyte is cultured under these conditions for about 4–10 days, and, during the culture, the culture medium may be successively refreshed to supplement sufficient amounts of nutrients, as well as to wash, and/or dilute the metabolites released in the culture medium.

For in vivo proliferation, the human myelomonocytes can be implanted into a non-human warm-blooded animal or placing the cells into a diffusion chamber in which the cells can be suppled with the nutrient body fluid of the animal, and feeding the animal in the usual manner. The in vivo proliferation provides a larger amount of human myelomonocyte IFN-gamma with the same amount or much less nutrient culture medium containing expensive serum than does the in vitro tissue culture.

The in vivo proliferation has the additional advantages that it reduces the care required during cell proliferation, it stabilizes cell proliferation, and it augments the amount of human IFN-gamma produced per cell, by up to two- to ten-fold more.

The non-human warm-blooded animals which can be used for the in vivo proliferation are those animals in which human myelomonocytes proliferate, including fowls such as chickens and pigeons, mammals such as dogs, cats, monkeys, goats, pigs, cows, horses, rabbits, guinea pigs, rats, hamsters, mice and nude mice.

Since implantation of human myelomonocytes may elicit an undesirable immunoreaction in the animal, it is desirable to use an animal in the youngest possible stage, for example, egg, embryo or fetus, or a newborn or infant animal. Use of such young animals reduces the immunoreaction to the lowest possible level.

The animal may be irradiated with X-rays or gamma-rays, about 200–600 rem, or injected with an antiserum or an immunosuppressant prior to implantation, also to reduce the immunoreaction.

When the nude mouse is used, human myelomonocytes can be implanted without pretreatment and proliferated readily with less fear of causing undesirable immunoreaction because the nude mouse elicits less immunoreaction, even in adulthood.

The cell proliferation can be stabilized and/or the production of human IFN-gamma by human myelomonocyte can be augmented by successive implantation using the same or different non-human warm-blooded animals. These objects can be effected, for example by first implanting and proliferating human myelomonocytes in hamsters, then successively implanting the proliferated cells in nude mice. This implantation can be carried out with non-human warm-blooded animals of the same class or order, as well as those of the same species or genus.

Human myelomonocytes can be implanted in any site of the animal as long as the cell proliferates in the h site. Examples of these locations include the allantoic cavity, intravenously, intraperitoneally, or subcutaneously.

Alternatively, human myelomonocytes can be proliferated by placing the cells into a conventional diffusion chamber of any desirable shape or size, equipped with an appropriate means to exclude the animal's cells but supplies to the cells (HBL-38) the nutrient body fluid from a non-human warm-blooded animal. Examples include membrane filters, ultrafilters, or hollow fibers, which have a pore size of about $10^{-7}$ to $10^{-5}$ m; embedding, for example intraperitoneally, the chamber in a non-human warm-blooded animal; and allowing the cell to proliferate in the chamber while allowing the cell to receive the nutrient body fluid from the animal.

The diffusion chamber can be arranged and placed, for example, on the animal, in such manner that the nutrient fluid in the diffusion chamber can freely circulate therethrough. The diffusion chamber can be arranged in such a manner that the culture can be observed during the cell proliferation through the chamber wall. Alternatively, a diffusion chamber can be replaced at intervals with a fresh one to continue the cell proliferation over the life span of the animal without sacrifice, as well as to augment much more the cell production per animal.

Since, in the diffusion chamber method, the human myelomonocyte never contacts the animal cell and elicits much less undesirable immunoreaction, any non-human warm-blooded animal can be freely used without pretreatment to reduce immunoreaction, and the proliferated cells can be recovered easily.

The animal is fed in the usual manner, and no special care is required even after implantation. The period for maximum cell proliferation is usually from 1–10 weeks. The number of myelomonocytes obtained is about $10^7$ to $10^{12}$ cells per animal or more. More particularly, according to the present invention, the implanted myelomonocytes increase about $10^2$ to $10^7$-fold or more, which is about $10$–$10^6$-fold or more than the increase obtained by inoculating and proliferating myelomonocytes on an in vitro nutrient culture medium. This is very useful in preparing human myelomonocyte IFN-gamma.

Any induction method can be used in the present invention as long as it induces production of human myelomonocyte IFN-gamma in human myelomonocytes obtained in this manner. The human myelomonocytes can be exposed to the action of an IFN-gamma inducer in the animal used for proliferation. For example, a human myelomonocyte proliferated in ascites fluid in suspension, or a tumor formed, for example, subcutaneously, is exposed directly to an IFN-gamma inducer, and the resultant human myelomonocyte IFN-gamma is recovered from the ascite, serum and/or tumor, followed by purification.

The proliferated human myelomonocyte can be recovered from the animal, and then exposed in vitro to an IFN-gamma inducer. For example, a human myelomonocyte obtained by recovery from ascite, fluid or extraction and disaggregation of the tumor mass formed, subcutaneously, for example, is suspended in a nutrient culture medium kept at about 20°–40° C. to give a cell density of about $10^5$–$10^8$ cells/ml, and exposed to an IFN-gamma inducer. The resulting human myelomonocyte IFN-gamma is then recovered and purified.

When a diffusion chamber is used, human myelomonocytes can be exposed to an IFN-gamma inducer in the diffusion chamber or after recovery therefrom.

The priming method using HuIFN and or the super-induction method using antimetabolite can be used to further augment the production of human myelomonocyte IFN-gamma.

The amount of production of human myelomonocyte IFN-gamma per animal may be still further increased by using one or more of the following methods:

(1) Human myelomonocytes are exposed to an IFN-gamma inducer in the animal, recovered from a certain site in the animal or its whole body, and exposed in vitro to IFN-gamma inducer;

(2) Human myelomonocyte is repeatedly exposed to an IFN-gamma inducer; and (3) The diffusion chamber embedded in or connected to the animal is replaced at intervals with a fresh chamber.

The IFN-gamma inducers which can be used in the present invention are usually mitogens, such as phytohemagglutinin, concanavalin A, pokeweed mitogen, lipopolysaccharide, endotoxin, lipid A, polysaccharide and bacteria.

Antigens act as IFN-gamma inducers on sensitized cells. The IFN-gamma inducer are generally used at a concentration of from about 0.001 µg/ml to 19 mg/ml. The use of an IFN-alpha inducers, such as a virus, nucleic acid, or polynucleotide, may increase the production of human myelomonocyte IFN-gamma and/or induction of simultaneous production of HuIFN-alpha.

The human myelomonocyte IFN-gamma can be recovered using one or more conventional purification and separation methods. Examples of these methods include salting out, dialysis, filtration, centrifugation, concentration and lyophilization. When further purification is required, one or more conventional procedures may be employed to effect this purification. Examples of these further procedures include adsorption and desorption with ion exchange, gel filtration, isoelectric point fractionation, electrophoresis, ion exchange chromatography, high-performance liquid chromatography, column chromatography and affinity chromatography. Any combination of these methods may be used. Chromatography using a monoclonal antibody produces a human myelomonocyte IFN-gamma of the highest purity, i.e., up to about $10^8$ units/mg protein, and usually $1 \times 10^7$ to $3 \times 10^7$ units/mg protein.

The human myelomonocyte IFN-gamma thus obtained can be advantageously used for preventing and treating diseases that are susceptible to prevention and treatment by HuIFN-gamma.

"HuIFN-gamma susceptible diseases" means those diseases which can be prevented or treated with human myelomonocyte IFN-gamma. These diseases include viral diseases such as epidemic conjunctivitis, herpetic keratitis, influenza, rubella, serum hepatitis, and acquired immune deficiency syndrome (AIDS); as well as nonviral diseases including malignant tumors such as colon carcinoma, lung carcinoma, liver carcinoma and osteosarcoma; immunopathies including atopic allergy, myasthenia, collagenosis, pernicious anemia, articular rheumatism, and systemic lupus erythematosus.

The IFN-gamma of the present invention can be formulated into an appropriate composition for its final uses. Some of these formulations include nebulae, collyrium, colutory, an injectable liquid, a paste medicine such as an ointment, and solid medicine forms such as powders, granules and tablets.

The human myelomonocyte IFN-gamma is usually present in the formulations in the range of 1–10,000 units/g. The efficacy of the active ingredient can be augmented by combining one or more lymphokines such as HuIFN-alpha, HuIFN-beta, tumor necrosis factor (TNF), lymphotoxin, interleukin 2, and B-cell differentiating factor, or natural or synthetic chemotherapeutics.

The human myelomonocyte IFN-gamma can be used in combination with adjuvants, fillers, and/or stabilizers. The compositions thus prepared are suitable for use as antiviral agents, antioncotics, enhancers for antioncotics, agents for depressing metastasis of malignant tumors, suppressants for palindromia, as imunoregulators, as therapeutic agents for rheumatism, and as therapeutic agents for immunopathy.

The activity of HuIFN was determined with the plaque reduction method using FL cells derived from human amniotic fluid as described in *Protein, Nucleic Acid and Enzyme*, Vol. 20, NO. 6, pp. 616–643 (1975).

The hemagglutination titer was determined in accordance with the method as described in J. E. Salk, *The Journal of Immunology*, Vol. 49, pp. 87098 (1944).

HBL-38 cells established by the present inventors will hereinafter be described.

A leukocyte from an acute myeloleukemia patient of 55 years of age, after culturing on in vitro nutrient, began proliferation on the 21st day. The leukocyte was repeatedly subcultured, and the present inventors eventually succeeded in stably proliferating one of the subcultures. This subculture was named "HBL-38."

(1) Proliferation

Doubling time on RPMI 1640 medium supplemented with 10 v/v % fetal calf serum was about 30 hours.

(2) Morphology

HBL-38 cells tended to attach to the inside bottom of the flask during proliferation, but the attachment was loose and the cell was easily detached. Although cell clumps were formed during proliferation, these clumps were not rigid and they were easily disaggregated. The result of phase-contrast microscopic observation was as shown in FIG. 1. The cells were regularly rounded, and had a thickness of about 15 micrometers. The Giemsa's stain revealed that the nuclei were rounded, with an occasional irregular lobation or a laryolobism.

shown in Table II. Analysis using goat erythrocytes (E), erythrocyte amboceptors (EA) and erythrocyte amboceptor complement (EAC) revealed that EA formed 10% rosette but the others did not Detection of surface immunoglobulins (SmIg) using six anti-human goat antibodies revealed that HBL-38 cells were negative to all of these antibodies. Screening of surface markers using monoclonal antibodies revealed that 3A1, MCS-2, B3/25 and MY-9 exerted a relatively high positive effect, but NU-T2, Leu-5, Leu-4, A-50, BA-2, OKI-1, NU-N1, B2, MO-1 and MO-2 were negative.

(6) Screening of EB virus determined nuclear antigen (EBNA)

HBL-38 cells were screened for EBNA several times from an early stage of the establishment. The results revealed that HBL-38 cells were EBNA-negative.

(7) Colony formation on soft agar medium

HBL-38 cells were tested for colony formation in 0.3% agar medium containing colony stimulating factor (CSF). Inverted-microscopic observation on the 14th day revealed the presence of a colony-forming myeloid cell. The frequency was 1 to 2%. No colony was formed when no CSF was added.

Based on the above data, HBL-38 cells were deemed to be myelomonocytes.

TABLE II

Marker profile
Surface markers

| (Standard) | | | | | | | | | |
|---|---|---|---|---|---|---|---|---|---|
| | | | | | SmIg | | | | |
| E | EA | EAC | κ | λ | α | δ | γ | μ | |
| 0 | 10 | 0 | 0 | 0 | 0 | 0 | 0 | 0 | |
| (Monoclonal antibody) | | | | | | | | | |
| NU-T2 | Leu-5 | Leu-4 | Leu-3a | A50 | 3A1 | Leu-2a | BA2 | NU-N1 | Tac | OKM-1 | MCS-1 |
| 0 | 0 | 0 | 10 | 0 | 90 | 10 | 0 | 0 | 10 | 10 | 20 |
| MCS-2 | MY-1 | MY-9 | MO-1 | CA-2-38 | MO-2 | B7/21 | OKI-1 | B3/25 | A3/10 | B2 | |
| 100 | 10 | 70 | 0 | 40 | 0 | 10 | 60 | 100 | 60 | 0 | |
| | | | | Virus marker EBV | | | | | | | |
| | | | | — | | | | | | | |

Note: The values indicate positiveness (%).

(3) Chromosome number

Chromosome analysis was conducted with cells in exponential growth. The frequency distribution of chromosome numbers was as shown in Table I. Observation of 150 chromosomes revealed that the chromosome numbers were in a low diploid region and the most frequent distribution was 45 (53 chromosomes). Forty-two cells had a chromosome number of 44.

TABLE I

Frequency distribution of chromosome number

| Chromosome number | 31 | 32 | 36 | 40 | 41 | 42 | 43 | 44 | 45 | 46 | 47 | 48 | 49 | 50 |
|---|---|---|---|---|---|---|---|---|---|---|---|---|---|---|
| Cell number | 1 | 1 | 1 | 1 | 7 | 6 | 11 | 42 | 53 | 14 | 7 | 5 | 1 | 0 |

(4) Karyotypic analysis

Figure 2:
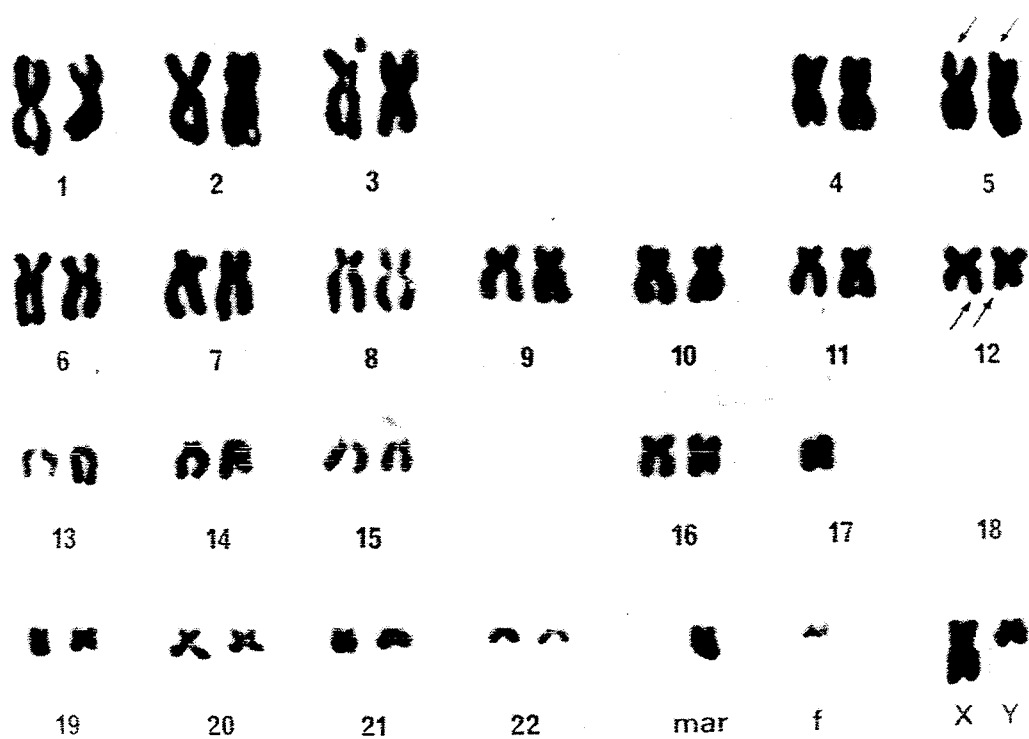
FIG. 2 shows the results of karyotypic analysis of HBL-38 cells.

The results of karyotypic analysis were as shown in FIG. 2. The sex chromosome was XY, and this was consistent with that of the cell source. One counterpart of chromosome 17 and the whole of chromosome 18 were missing. It was found that a chromosome was inserted respectively in a short arm (p) of chromosome 5 and a long arm (g) of chromosome 12. An unidentifiable marker chromosome and a chromatid were observed.

(5) Cell surface character

Identification of HBL-38 cells was carried out with various cell surface antibodies, and the results were as The following experiments illustrate preparing human myelomonocyte IFN-gamma.

EXPERIMENT 1

Comparison of established human lymphoblastoid cells on HuIFN-gamma production

EXPERIMENT 1-1

HuIFN production by in vitro proliferated cells

An established human lymphoblastoid cell was inoculated to RPMI 1640 medium (pH 7.2) supplemented with 20% fetal calf serum, and the mixture was cultured at 37° C. in the conventional manner. The resultant culture was washed with serum-free RPMI 1640 medium (pH 7.2), and then suspended with a fresh preparation of the same culture medium to $1 \times 10^6$ cells/ml.

The resultant cell suspension was added with about 10 μg/ml of lipopolysaccharide, an the mixture was kept at 37° C. for two days to induce HuIFN production. The culture was centrifugally separated, and the supernatant was determined for total HuIFN and human IFN-gamma activities.

The results were as shown in Table III.

As evident from these data, it was found that human myelomonocytes was HuIFN-gamma producible and the production was higher than those attained with the established human lymphoblastoid cells tested. HBL-38 cells were extremely high in HuIFN-gamma production.

TABLE III

| T cell | | | |
|---|---|---|---|
| CCRF-CEM | TALL-1 | MOLT-3 | KE-37 |
| below 100 | below 100 | below 100 | below 100 |
| B cell | | | |
| NALM-1 | KLM-2 | Namalwa | BALL-1 |
| below 20 | below 20 | below 20 | below 20 |
| Non T · non B cell | | | |
| KM-3 | NALL-1 | KOPN-K | BV-173 |
| below 20 | below 20 | below 20 | below 20 |
| Non L · non M cell | | | |
| K-562 | HEL | SPI-801 | L-428 |
| below 20 | below 20 | below 20 | below 20 |
| Myelomonocyte | | | |
| HBL-38 | | KG-1 | |
| 3,800 (3,200) | | 1,600 (1,400) | |

Note: The values indicate HuIFN activity; and those in the parentheses, HuIFN-gamma activity.

EXPERIMENT 1-2

HuIFN production by in vivo proliferated cells

Newborn hamster were injected with an antiserum prepared from rabbits in the usual manner to weaken possible immunoreaction, implanted subcutaneously with an established human myelomonocyte, and fed for three weeks in the usual manner. The tumor masses formed in the body of the hamsters were extracted and disaggregated by suspension in trypsin-containing saline.

As suspension of the cells obtained was treated and analyzed for total HuIFN and HuIFN-gamma activities as in Experiment 1-1

The results were as shown in Table IV.

TABLE IV

| HuIFN production by myelomonocyte | |
|---|---|
| HBL-38 | KG-1 |
| HuIFN (HuIFN-gamma) | HuIFN (HuIFN-gamma) |
| 66,000 (59,000) | 31,000 (25,000) |

The data in Tables III and IV confirmed that established human myelomonocytes, specifically, HBL-38 cells, produced greater quantities of HuIFN-gamma when proliferated in vivo rather than in vitro.

The following examples illustrate preparation of human myelomonocyte IFN-gamma.

Example A-1

HBL-38 cells were inoculated on RPMI 1640 medium (pH 7.2), supplemented with 10 v/v % fetal calf serum, to $5 \times 10^5$ cells/ml.

The resultant mixture was cultured at 37° C. while the culture medium was periodically refreshed. Thereafter, by using a fresh preparation of the same culture medium, the cells were washed and suspended at $2 \times 10^6$ cells/ml. To the cell suspension was added about 10 µg/ml lipopolysaccharide, and the mixture was maintained at 37° C. for two days to induce HuIFN production. The resultant cultures was separated centrifugally and a supernatant containing about 5100 units of human myelomonocyte IFN-gamma per ml was obtained.

Example A-2

Newborn hamsters were injected with an antiserum prepared from rabbits in the usual manner to weaken possible immunoreactions, HBL-38 cells were implanted subcutaneously, and the hamsters were fed for four weeks in the usual manner. Tumor masses of about 20 g each formed in the animals. These tumor masses were extracted and disaggregated by suspension in saline containing collagenase.

After washing with Eagle's minimal essential medium, the cells were diluted with a fresh preparation of the same culture medium to about $2 \times 10^6$ cells/ml, and 200 µg, ml of phytohemagglutinin and 5 g/ml lipid A were added. The mixture was maintained at 37° C. for two days to induce production of human myelomonocytes. The resultant culture was separated by centrifugation to obtain a supernatant containing about 93,000 units of human myelomonocyte IFN-gamma. Thus, about 183,000,000 units of human myelomonocyte IFN-gamma were obtained per hamster.

Example A-3

KG-1 cells were intravenously implanted into newborn rats. The rats were fed for four weeks in the usual manner.

Tumor masses of about 20 grams each were formed in the animals. These tumor masses were extracted and disaggregated as in Example A-2 to obtain a cell suspension. To the cell suspension were added about 100 hemagglutination titers/ml of Sendai virus and about 5 µg/ml lipopolysaccharide, and the mixture was incubated at 37° C. for two days to induce production of human myelomonocyte IFN. The resultant culture was separated by centrifugation to obtain a supernatant containing about 49,000 units of human myelomonocyte IFN-gamma per ml. The yield of human myelomonocyte IFN-gamma was about 97,000,000 units per rat.

Example A-4

CTV-1 cells were suspended with saline in 10 ml plastic cylinder diffusion chambers equipped with a membrane filter, pore size of about 0.5 microns, and the diffusion chambers were embedded intraperitoneally in adult rats.

The rats were fed for four weeks in the usual manner, and the chambers were removed.

The proliferated cells were treated as in Example A-1 to induce production of human myelomonocyte IFN. The resultant culture was separated by centrifugation to obtain a supernatant containing about 41,000 units of human myelomonocyte IFN-gamma per ml. The yield was about 78,000,000 units per rat.

Example A-5

HBL-38 cells were implanted into embryonated eggs, and the eggs were incubated at 37° C. for an additional week. The proliferated cells were recovered by breaking the eggs, and the cells were treated as in Example A-2 to induce production of human myelomonocyte IFN. The resultant culture was centrifugally separated to obtain a supernatant containing about 46,000 units of human myelomonocyte IFN-gamma per ml. The yield was about 60,000,000 units per 10 eggs.

The following Examples illustrate methods for preparing monoclonal anti-HuIFN-gamma antibody and purifying human myelomonocyte IFN-gamma using this monoclonal antibody.

Example B-1(1)

Preparation of a partially purified human myelomonocyte IFN-gamma

A liquid containing human myelomonocyte IFN-gamma prepared by the method of Example A-2 was dialyzed against 0.01M Tris-phosphate buffer (pH 8.5) for 20 hours, and then membrane filtered. The filtrate was applied to an antibody column binding anti-HuIFN-alpha- and anti-HuIFN-beta-antibodies, and the non-adsorbed fraction was recovered. The fraction was chromatofocused to obtain a fraction with an antiviral activity which was then concentrated and lyophilized to obtain a powder containing human myelomonocyte IFN-gamma in an activity yield of about 30%. The specific activity of the powder was about $10^6$ units/mg protein.

Example B-1(2)

Preparation of monoclonal anti-HuIFN-gamma antibody

A partially purified human myelomonocyte IFN-gamma obtained by the method of Example B-1(1) was dissolved in saline to a concentration of about 0.05 w/w %, and to the resultant solution was added an equivalent volume of Freund's complete adjuvant. Mice were injected intravenously with 0.2 ml aliquots of the mixture, and were reinjected on the 7th day after the first injection to effect immunization. The spleens in which anti-HuIFN-gamma production had been induced in the antibody producing cells were extracted from the mice, minced and disaggregarted, after which the spleen cells were suspended together with $P_3$-X63-Ag8 cells, mouse myeloma cells purchased from Flow Laboratories, Maryland, USA, in 37° C. serum-free Eagle's minimum essential medium (pH 7.2) containing 50 w/v % polyethylene glycol 1000 to give a respective cell density of $10^4$ cells/ml. After standing for five minutes, the cell suspension was diluted 20 times in a fresh preparation of the same culture medium, and the hybrid cells capable of growing on the hypoxanthine, aminopterin, thymidine containing medium were recovered and cloned in accordance with the method as reported in R. L. Davidson and P. S. Gerald, *Somatic Cell Genetics*, Vol. 2, No. 2, pp. 175–176 (1976) to obtain a hybrid cell capable of producing anti-HuIFN-gamma antibody. The hybrid cells were then implanted intraperitoneally in mice at a dosage of about $10^6$ cells per mouse, and the mice were fed for two weeks and then sacrificed. The body fluids recovered from the mice, such as ascite and blood, were separated centrifugally to obtain a supernatant to which was then added ammonium sulfate to 30-50% saturation. The resultant sediment was dialyzed and affinity-chromatographed with an immobilized HuIFN-gamma that had been obtained by the method of Example B-1(1) with BrCN-activated Sepharose. The anti-HuIFN antibody fraction obtained was dialyzed, concentrated and lyophilized into powder.

The product obtained above immunologically neutralized a human myelomonocyte IFN-gamma derived from human myelomonocyte.

The stability of the monoclonal antibody in aqueous solution was determined by measuring the residual neutralizing activity upon incubation for thirty minutes at pH 7.2. As a result, the monoclonal antibody retained over 80% activity when incubated at 60° C., but lost over 90% activity when incubated at 70° C. Upon incubation for sixteen hours at 4° C., the monoclonal antibody was found to be table at a pH in the range of 4.0–11.0, but lost over 90% of its activity at pH 2.0.

Further investigation revealed that the monoclonal antibody was unstable in the presence of 2-mercaptoethanol and caused an antigen-antibody reaction specifically with anti-mouse immunoglobulin M antibody.

This confirmed that the monoclonal antibody was a class M immunoglobulin antibody.

Example B-1(3)

Preparation of highly purified human myelomonocyte IFN-gamma

A partially purified human myelomonocyte IFN-gamma prepared by the method of Example B-1(1) was chromatographed onto a column of an immobilized monoclonal antibody gel prepared by the method of Example B-1(2), and the fraction with human myelomonocyte IFN-gamma activity was recovered, dialyzed, concentrated and lyophilized to obtain a solid containing human myelomonocyte IFN-gamma in a yield of about 80%. The product was a very pure human myelomonocyte IFN-gamma, and the specific activity was about $1.5 \times 10^7$ units/mg protein.

Example B-2

Example B-2(1)

Preparation of partially purified human myelomonocyte IFN-gamma

A solution containing a human myelomonocyte IFN-gamma prepared by the method of Example A-3 was partially purified in accordance with the method of Example B-1(1) to obtain a human myelomonocyte IFN-gamma preparation with a specific activity of about $10^6$ units/mg protein in a yield of about 20%.

Example B-2(2)

Preparation of monoclonal anti-Hu-IFN-gamma antibody

Spleen cells were obtained by immunizing mice as in Example B-1(2), except that the partially purified human myelomonocyte IFN-gamma obtained in Example B-2(1) was used as the antigen.

The spleen cells were suspended together with P3-NS-1/1-Ag4 cells, mouse myeloma cells purchased from Dainippon Pharmaceutical Co., Ltd., Osaka, Japan in a salt solution containing 140 mM NaCl, 54 mM KCl, 1 mM $NaH_2PO_4$ and 2 mM $CaCl_2$. The suspension had a cell density of $10^4$ cells/ml. To the cell suspension was added, under ice-chilled conditions, a fresh preparation of the same salt solution additionally containing a UV-irradiated inactivated Sendai virus, and the mixture was diluted about 20 times after a period of five minutes in 37° C. RPMI 1640 medium. A hybrid cell capable of producing anti-HuIFN-gamma antibody was cloned by treating the diluted mixture as in Example B-1(2).

The hybrid cells obtained were implanted intraperitoneally in seven day old hamsters whose immunoreaction had been weakened in conventional manner. The dosage was about $10^7$ cells per hamster, and the hamsters were treated as in Example B-1(2) to obtain a monoclonal antibody.

The product obtained from the above immunologically neutralized a human myelomonocyte IFN-gamma derived as in Example B-1(2).

The stability of the monoclonal antibody in aqueous solution was determined by measuring the residual neutralizing activity upon incubation for thirty minutes at pH 7.2. It was found that the monoclonal antibody retained over 80% activity when incubated at 60° C., but lost over 90% of its activity when incubated at 70° C. After incubating for 16 hours at 4° C., the monoclonal antibody was found to be stable at a pH in the range of 2.0–11.0

Further investigation revealed that the monoclonal antibody was stable in the presence of 2-mercaptoethanol, and caused an antigen-antibody reaction specifically with anti-mouse immunoglobulin G antibody.

This confirmed that the monoclonal antibody was an immunoglobulin G antibody.

Example B-2(3)

Preparation of a highly purified human myelomonocyte IFN-gamma

A partially purified human myelomonocyte IFN-gamma prepared by the method of Example B-2(1) was chromatographed onto a column of an immobilized monoclonal antibody prepared by the method of Example B-2(2). The fraction containing human myelomonocyte IFN-gamma was recovered, dialyzed and concentrated to obtain a liquid containing human myelomonocyte IFN-gamma in an activity yield of about 85%. The product was a highly purified human myelomonocyte IFN-gamma, and the specific activity was about $1.5 \times 10^7$ units/mg protein.

Example B-3

A filtrate obtained by dialyzing a human myelomonocyte IFN-gamma containing supernatant, obtained by the method of Example A-1, was dialyzed against saline containing 0.01M phosphate buffer (pH 7.2) for fifteen hours, and the resultant supernatant was membrane-filtered. The filtrate was purified on an antibody column in accordance with the method of Example B-1(3), concentrated, and lyophilized to yield a solid containing human myelomonocyte IFN-gamma in an activity yield of about 75%. The product was a highly purified human myelomonocyte IFN-gamma, and the specific activity was about $1.5 \times 10^7$ units/mg protein.

Example B-4

A human myelomonocyte IFN-gamma containing supernatant obtained by the method of Example A-4 was dialyzed and membrane-filtered in accordance with the method of Example B-3. The resultant filtrate was purified on an antibody column and concentrated as in Example B-2(3) to yield a solution containing human myelomonocyte IFN-gamma in an activity yield of about 70%. The product was a highly purified human myelomonocyte IFN-gamma, and the specific activity of the product was about $1.5 \times 10^7$ units/mg protein.

Example B-5

A human myelomonocyte IFN-gamma containing supernatant contained by the method of Example A-5 was dialyzed and membrane-filtered in accordance with the method of Example B-3. The resultant filtrate was purified on an antibody column, concentrated and lyophilized in a manner similar to that of Example B-1(3) to obtain a solid containing human myelomonocyte IFN-gamma in an activity yield of about 70%. The product was a highly purified human myelomonocyte IFN-gamma, and the specific activity of the product was about $1.5 \times 10^7$ units/mg protein.

Experiment 2

Physicochemical properties of human myelomonocyte IFN-gamma

Experiment 2-1

Molecular weight of human myelomonocyte IFN-gamma

A highly purified human myelomonocyte IFN-gamma prepared by the method of Example B-1(3) was subjected to SDS-polyacrylamide gel electrophoresis in accordance with the method described by U. K. Lasemmli in *Nature*, Vol. 227, pp. 680–685 (1970). Several bands were observed around the molecular weight of about 24,000; 20,000 and 16,000 daltons. The amount of protein in the bands was about 7:2:1 based upon their respective molecular ratios. HuIFN-gamma activity was detected in each band. Furthermore, the presence of carbohydrate chains was verified by periodic acid Schiff base stain in accordance with the method described by R. A. Kapitany and E. J. Zebrowski in *Analytical Biochemistry*, Vol. 56, pp. 361–369 (1973). The bands having a molecular weight of about 24,000 and 20,000 daltons were positive.

Experiment 2-2

Amino acid sequence of human myelomonocyte IFN-gamma

The amino acid sequence of a highly purified human myelomonocyte IFN-gamma, prepared by the method of Example B-1(3), was determined in accordance with the method described by Ernst Rinderknecht et al. in *The Journal of Biological Chemistry*, Vol. 259, No. 11, pp. 6790–6797 (1984).

The human myelomonocyte IFN-gamma was digested with trypsin or V8 protease, a product of Sigma Chemical Company, St. Louis, Mo., USA, and the resultant peptide fragments were fractionated with high-performance liquid chromatography. Each fragment was fed to a Model 470A gas phase protein sequencer, commercialized by Applied Biosystems, Inc., California, U.S.A., and then analyzed with high performance liquid chromatography to determine the amino acid sequence of human myelomonocyte IFN-gamma. Carbohydrate chains coupled to peptide fragments were first cut with glycopeptidase A, a product of Seikagaku Kogyo Kabushiki Kaisha, Tokyo, Japan, and then fed to a gas phase protein sequencer.

The evidence confirmed that the present human myelomonocyte IFN-gamma had main structure of the following polypeptide chain:

Formula I:

1 10
pyroGlu Asp Pro Tyr Val Lys Glu Ala Glu Asn Leu Lys Lys Tyr Phe 20 30
Asn Ala Gly His Ser Asp Val Ala Asp Asn Gly Thr Leu Phe Leu 40
Gly Ile Leu Lys Asn Trp Lys Glu Glu Ser Asp Arg Lys Ile Met -continued

```
           50                              60
Gln Ser Gln Ile Val Ser Phe Tyr Phe Lys Leu Phe Lys Asn Phe

70
Lys Asp Asp Gln Ser Ile Gln Lys Ser Val Glu Thr Ile Lys Glu 80                             90
Asp Met Asn Val Lys Phe Phe Asn Ser Asn Lys Lys Lys Arg Asp

100
Asp Phe Glu Lys Leu Thr Asn Tyr Ser Val Thr Asp Leu Asn Val 110                            120
Gln Arg Lys Ala Ile His Glu Leu Ile Gln Val Met Ala Glu Leu

130
Ser Pro Ala Ala Lys Thr Gly Lys Arg Lys Arg Ser Gln Met Leu

Phe Arg Gly
```

Formula II:

```
  1                                       10
pyroGlu Asp Pro Tyr Val Lys Glu Ala Glu Asn Leu Lys Lys Tyr Phe 20                             30
Asn Ala Gly His Ser Asp Val Ala Asp Asn Gly Thr Leu Phe Leu 40
Gly Ile Leu Lys Asn Trp Lys Glu Glu Ser Asp Arg Lys Ile Met 50                             60
Gln Ser Gln Ile Val Ser Phe Tyr Phe Lys Leu Phe Lys Asn Phe 70
Lys Asp Asp Gln Ser Ile Gln Lys Ser Val Glu Thr Ile Lys Glu 80                             90
Asp Met Asn Val Lys Phe Phe Asn Ser Asn Lys Lys Lys Arg Asp 100
Asp Phe Glu Lys Leu Thr Asn Tyr Ser Val Thr Asp Leu Asn Val 110                            120
Gln Arg Lys Ala Ile His Glu Leu Ile Gln Val Met Ala Glu Leu Ser Pro Ala Ala Lys Thr Gly Lys Arg
```

Formula III:

```
  1                                       10
pyroGlu Asp Pro Tyr Val Lys Glu Ala Glu Asn Leu Lys Lys Tyr Phe 20                             30
Asn Ala Gly His Ser Asp Val Ala Asp Asn Gly Thr Leu Phe Leu 40
Gly Ile Leu Lys Asn Trp Lys Glu Glu Ser Asp Arg Lys Ile Met 50                             60
Gln Ser Gln Ile Val Ser Phe Tyr Phe Lys Leu Phe Lys Asn Phe 70
Lys Asp Asp Gln Ser Ile Gln Lys Ser Val Glu Thr Ile Lys Glu 80                             90
Asp Met Asn Val Lys Phe Phe Asn Ser Asn Lys Lys Lys Arg Asp 100
Asp Phe Glu Lys Leu Thr Asn Tyr Ser Val Thr Asp Leu Asn Val 110                            120
Gln Arg Lys Ala Ile His Glu Leu Ile Gln Val Met Ala Glu Leu Ser Pro Ala Ala Lys Thr Gly Lys
```

Formula IV:

```
  1                                       10
pyroGlu Asp Pro Tyr Val Lys Glu Ala Glu Asn Leu Lys Lys Tyr Phe 20                             30
Asn Ala Gly His Ser Asp Val Ala Asp Asn Gly Thr Leu Phe Leu 40
Gly Ile Leu Lys Asn Trp Lys Glu Glu Ser Asp Arg Lys Ile Met 50                             60
Gln Ser Gln Ile Val Ser Phe Tyr Phe Lys Leu Phe Lys Asn Phe 70
Lys Asp Asp Gln Ser Ile Gln Lys Ser Val Glu Thr Ile Lys Glu 80                             90
Asp Met Asn Val Lys Phe Phe Asn Ser Asn Lys Lys Lys Arg Asp 100
Asp Phe Glu Lys Leu Thr Asn Tyr Ser Val Thr Asp Leu Asn Val 110                            120
Gln Arg Lys Ala Ile His Glu Leu Ile Gln Val Met Ala Glu Leu Ser Pro Ala Ala Lys Thr Gly, or
```

Formula V:

```
  1                                       10
pyroGlu Asp Pro Tyr Val Lys Glu Ala Glu Asn Leu Lys Lys Tyr Phe 20                             30
Asn Ala Gly His Ser Asp Val Ala Asp Asn Gly Thr Leu Phe Leu 40
Gly Ile Leu Lys Asn Trp Lys Glu Glu Ser Asp Arg Lys Ile Met 50                             60
Gln Ser Gln Ile Val Ser Phe Tyr Phe Lys Leu Phe Lys Asn Phe 70
Lys Asp Asp Gln Ser Ile Gln Lys Ser Val Glu Thr Ile Lys Glu 80                             90
Asp Met Asn Val Lys Phe Phe Asn Ser Asn Lys Lys Lys Arg Asp 100
Asp Phe Glu Lys Leu Thr Asn Tyr Ser Val Thr Asp Leu Asn Val 110                            120
Gln Arg Lys Ala Ile His Glu Leu Ile Gln Val Met Ala Glu Leu Ser Pro Ala Ala Lys Thr
```

In the above formula, a carbohydrate chain in the form of glycosylamine chains is coupled to either or both asparagines, which are located at the 25th and 97th positions from the $NH_2$ terminus of the polypeptide chain.

In other words, the polypeptide chain shown by Formula II lacks nine amino acids from the COOH terminus of the polypeptide chain shown by Formula I, and, similarly, the polypeptide chains shown by Formulas III, IV and V, respectively lack, 10, 11 and 12 amino acids form the COOH terminus of the polypeptide chain shown in Formula I. Specifically, it was also confirmed that the content of the polypeptide chain shown in Formula IV is relatively high, or about 50–80% based on the molecular ratios of these polypeptide chains.

Experiment 2–3

Carbohydrate structure of human myelomonocyte IFN-gamma

The carbohydrate chain structure of a highly purified human myelomonocyte IFN-gamma, prepared by the method of Example B-1(3), was studied.

Experiment 2-4(1)

Nonionic saccharide and amino sugar comprising the carbohydrate chain of human myelomonocyte IFN-gamma In accordance with the method described in *European Journal of Biochemistry*, Vol., 156, pp. 651-654 (1986), a human myelomonocyte IFN-gamma prepared by the method of Example B-1(3) was subjected to methanolysis, and the resultant compound was trimethylcylylated, after which it was subjected to gas chromatography for determination of a nonionic saccharide in the IFN-gamma. Furthermore, a human myelomonocyte IFN-gamma was first hydrolyzed with methanesulfonic acid in accordance with the method described by R. J. Simpson et al. in *The Journal of Biological Chemistry*, Vol. 251, No. 7, pp. 1936-1940 (1976). This hydrolyzate was then fed to an amino acid analyzer to determine the amino sugars of human myelomonocyte IFN-gamma according to the method described by A. M. Bella et al. in *Journal of Chromatography*, Vol. 51, pp. 314-351 (1970).

The results confirmed that both nonionic saccharides and amino sugars consisted of D-mannose, D-galactose, L-fucose and N-acetyl-D-glucosamine in a molecular ratio of 3.00:2.16:0.82:3.94.

Experiment 2-4(2)

Arrangement and coupling mode of carbohydrate chain in human myelomonocyte IFN-gamma In accordance with the method described by S. Hase et al. in *The Journal of Biochemistry*, Vol. 95, pp. 197-203 (1984), a human myelomonocyte IFN-gamma prepared by the method of Example B-1(3) was subjected to hydrazinolysis and pyridylamination, and the resulting compound was subjected to gel chromatography to remove excessive amounts of reagents to yield a pyridylamino sugar chain. The arrangement and coupling mode of a carbohydrate chain in the human myelomonocyte IFN-gamma was then determined.

Anion exchange chromatography revealed that the pyridylamino sugar contained a monosialylated oligosaccharide and a disialylated oligosaccharide.

Furthermore, the pyridylamino sugar was digested with neuraminidase to yield a disialylated pyridylamino sugar chain which was then fractionated according to molecular sizes by high performance liquid chromatography. Each fraction was successively degraded by exo-glycosidase to determine the arrangement of the carbohydrate chain of the human myelomonocyte IFN-gamma.

The pyridylamino sugar was fractionated by reverse-phase column chromatography, and the resultant fractions were respectively subjected to 500-MHz $^1$H-NMR spectroscopy to determine their coupling mode.

The results confirmed that the aforementioned polypeptide chain of the human myelomonocyte IFN-gamma was coupled to a carbohydrate chain shown by the following formula in the form of a glycosylamine type of chain:

Formula VI:

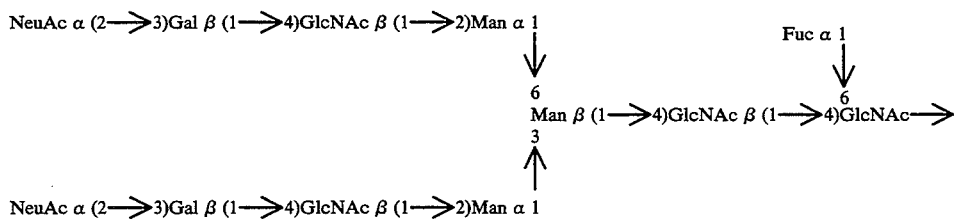

Formula VII:

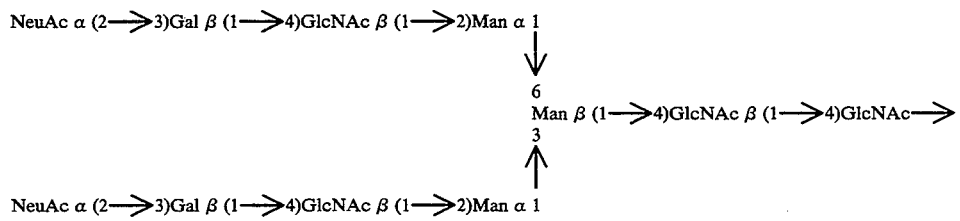

Formula VIII:

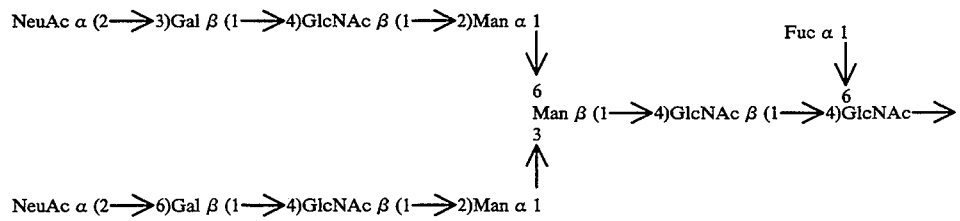

Formula IX:

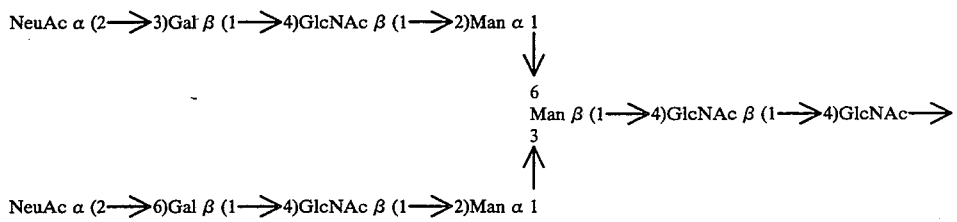

Formula X:

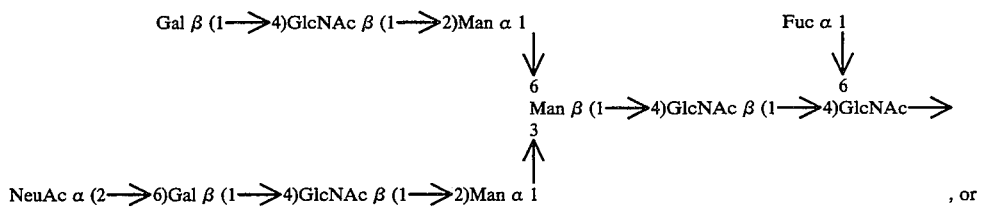

, or

Formula XI:

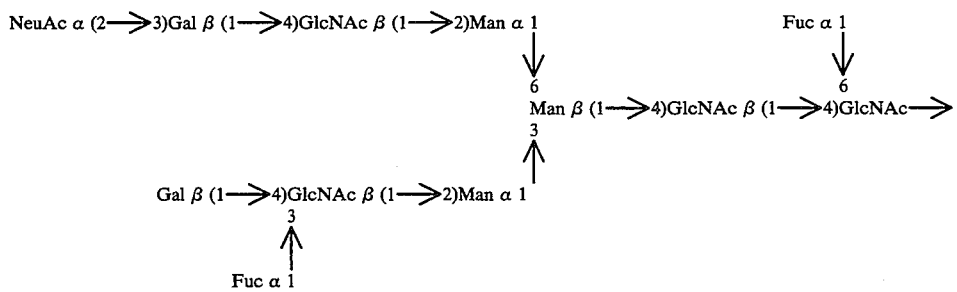

Wherein NeuAc, L1cNAc, G1cNAc, Gal, Man and Fuc mean N-acetylneuraminic acid, N-acetyl-D-glucosamine, D-galactose, D-mannose and L-fucose, respectively.

These structures of carbohydrate chains of human myelomonocyte IFN-gamma, which have not been found in IFN-alpha or IFN-beta, or in conventional HuIFN-gamma, such as those obtained from CHO cells and other cells, were found to be present in the substance of the present invention.

The content of these novel carbohydrate chains was relatively high, i.e., about 50–80% of the IFN-gamma, based upon a molecular ratio.

It was also found that the present human myelomonocyte IFN-gamma also contained a small amount of carbohydrate chain which had been found in a HuIFN-gamma derived from CHO cells.

The above result confirmed that the present human myelomonocyte IFN-gamma having a molecular weight of about 24,000 daltons has carbohydrate chains coupled to both asparagines which locate at the 25th and 97th positions with respect to the NH$_2$ terminus of the polypeptide chain, and the present myelomonocyte IFN-gamma having a molecular weight of about 20,000 daltons has a carbohydrate chain which is coupled to one of the asparagine.

In conclusion, the present human myelomonocyte IFN-gamma derived from a human myelomonocyte is a new HuIFN-gamma having a polypeptide chain for the main structure as shown by the following formula:

Formula I:

```
1                                                   10
pyroGlu Asp Pro Tyr Val Lys Glu Ala Glu Asn Leu Lys Lys Tyr Phe
                    20                              30
Asn Ala Gly His Ser Asp Val Ala Asp Asn Gly Thr Leu Phe Leu
                                    40
Gly Ile Leu Lys Asn Trp Lys Glu Glu Ser Asp Arg Lys Ile Met
                    50                              60
Gln Ser Gln Ile Val Ser Phe Tyr Phe Lys Leu Phe Lys Asn Phe
                                    70
Lys Asp Asp Gln Ser Ile Gln Lys Ser Val Glu Thr Ile Lys Glu
                    80                              90
Asp Met Asn Val Lys Phe Phe Asn Ser Asn Lys Lys Lys Arg Asp
                                    100
Asp Phe Glu Lys Leu Thr Asn Tyr Ser Val Thr Asp Leu Asn Val
                    110                             120
Gln Arg Lys Ala Ile His Glu Leu Ile Gln Val Met Ala Glu Leu
                                    130
Ser Pro Ala Ala Lys Thr Gly Lys Arg Lys Arg Ser Gln Met Leu
Phe Arg Gly
```

Formula II:

```
1                                                   10
pyroGlu Asp Pro Tyr Val Lys Glu Ala Glu Asn Leu Lys Lys Tyr Phe
                    20                              30
Asn Ala Gly His Ser Asp Val Ala Asp Asn Gly Thr Leu Phe Leu
                                    40
Gly Ile Leu Lys Asn Trp Lys Glu Glu Ser Asp Arg Lys Ile Met
                    50                              60
Gln Ser Gln Ile Val Ser Phe Tyr Phe Lys Leu Phe Lys Asn Phe
```

-continued

70
Lys Asp Asp Gln Ser Ile Gln Lys Ser Val Glu Thr Ile Lys Glu 80                                              90
Asp Met Asn Val Lys Phe Phe Asn Ser Asn Lys Lys Lys Arg Asp

100
Asp Phe Glu Lys Leu Thr Asn Tyr Ser Val Thr Asp Leu Asn Val 110                                             120
Gln Arg Lys Ala Ile His Glu Leu Ile Gln Val Met Ala Glu Leu

Ser Pro Ala Ala Lys Thr Gly Lys Arg

Formula III:

1                                               10
pyroGlu Asp Pro Tyr Val Lys Glu Ala Glu Asn Leu Lys Lys Tyr Phe 20                                              30
Asn Ala Gly His Ser Asp Val Ala Asp Asn Gly Thr Leu Phe Leu 40
Gly Ile Leu Lys Asn Trp Lys Glu Glu Ser Asp Arg Lys Ile Met 50                                              60
Gln Ser Gln Ile Val Ser Phe Tyr Phe Lys Leu Phe Lys Asn Phe 70
Lys Asp Asp Gln Ser Ile Gln Lys Ser Val Glu Thr Ile Lys Glu 80                                              90
Asp Met Asn Val Lys Phe Phe Asn Ser Asn Lys Lys Lys Arg Asp 100
Asp Phe Glu Lys Leu Thr Asn Tyr Ser Val Thr Asp Leu Asn Val 110                                             120
Gln Arg Lys Ala Ile His Glu Leu Ile Gln Val Met Ala Glu Leu Ser Pro Ala Ala Lys Thr Gly Lys Formula IV:

1                                               10
pyroGlu Asp Pro Tyr Val Lys Glu Ala Glu Asn Leu Lys Lys Tyr Phe 20                                              30
Asn Ala Gly His Ser Asp Val Ala Asp Asn Gly Thr Leu Phe Leu 40
Gly Ile Leu Lys Asn Trp Lys Glu Glu Ser Asp Arg Lys Ile Met -continued 50                                              60
Gln Ser Gln Ile Val Ser Phe Tyr Phe Lys Leu Phe Lys Asn Phe 70
Lys Asp Asp Gln Ser Ile Gln Lys Ser Val Glu Thr Ile Lys Glu 80                                              90
Asp Met Asn Val Lys Phe Phe Asn Ser Asn Lys Lys Lys Arg Asp 100
Asp Phe Glu Lys Leu Thr Asn Tyr Ser Val Thr Asp Leu Asn Val 110                                             120
Gln Arg Lys Ala Ile His Glu Leu Ile Gln Val Met Ala Glu Leu Ser Pro Ala Ala Lys Thr Gly, or Formula V:

1                                               10
pyroGlu Asp Pro Tyr Val Lys Glu Ala Glu Asn Leu Lys Lys Try Phe 20                                              30
Asn Ala Gly His Ser Asp Val Ala Asp Asn Gly Thr Leu Phe Leu 40
Gly Ile Leu Lys Asn Trp Lys Glu Glu Ser Asp Arg Lys Ile Met 50                                              60
Gln Ser Gln Ile Val Ser Phe Tyr Phe Lys Leu Phe Lys Asn Phe 70
Lys Asp Asp Gln Ser Ile Gln Lys Ser Val Glu Thr Ile Lys Glu 80                                              90
Asp Met Asn Val Lys Phe Phe Asn Ser Asn Lys Lys Lys Arg Asp 100
Asp Phe Glu Lys Leu Thr Asn Tyr Ser Val Thr Asp Leu Asn Val 110                                             120
Gln Arg Lys Ala Ile His Glu Leu Ile Gln Val Met Ala Glu Leu Ser Pro Ala Ala Lys Thr (wherein the abbreviations are commonly used for L-amino acids in the art)

wherein either or both of asparagines which locate at the twenty-fifth and ninety-seventh positions with respect to the NH$_2$ terminus of the polypeptide chain is coupled to a carbohydrate chain shown by Formula VI:

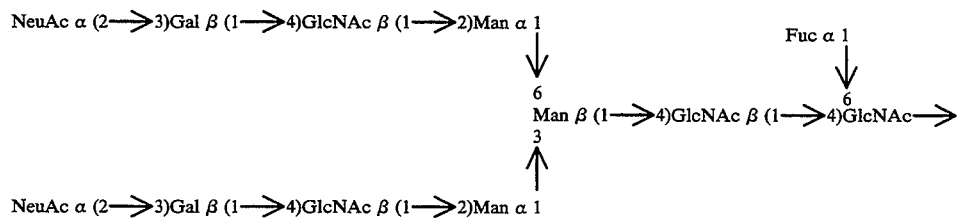

Formula VII:

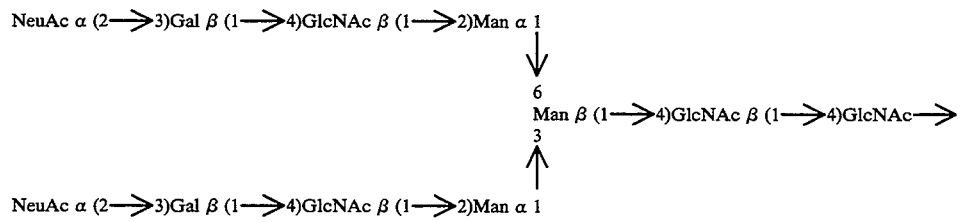

Formula VIII:

-continued

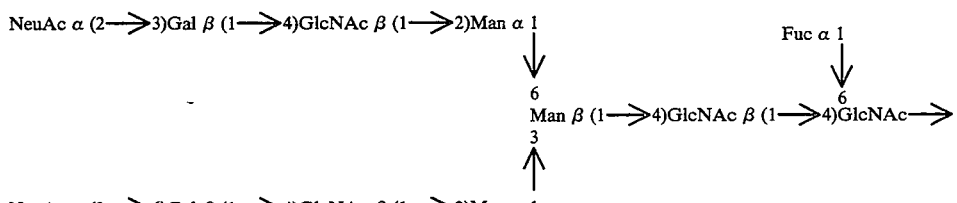

Formula IX:

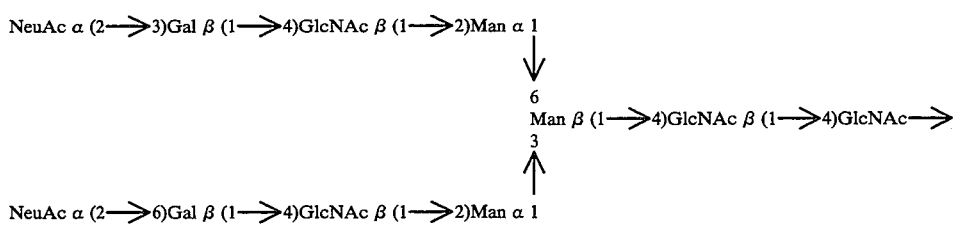

Formula X:

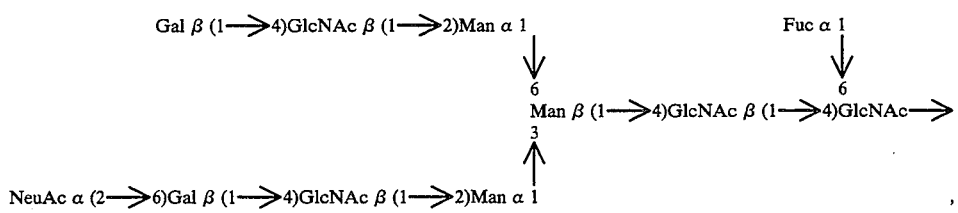

, or

Formula XI:

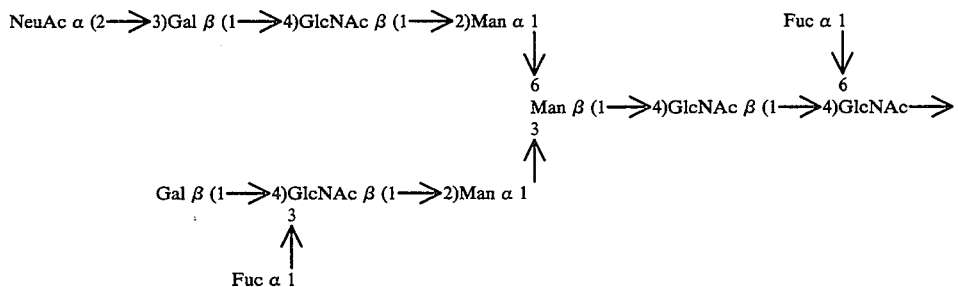

(wherein NeuAc, GlcNAc, Gal, Man and Fuc mean
N-acetylneuraminic acid, N-acetyl-D-glucosamine,
D-galactose, D-mannose and L-fucose respectively)

The product can be advantageously used as an effective component in therapeutic or prophylactic agents for viral diseases and malignant tumors, as well as a material for preparing HuIFN-gamma derivatives.

The product can be used as a component of prophylactic or therapeutic compositions for viral diseases and malignant tumors, as well as a material for preparing derivatives of HuIFN-gamma.

The following experiments illustrate preventing an treating HuIFN-gamma susceptible diseases using a human myelomonocyte IFN-gamma

Experiment 3

Prophylactic and therapeutic effects of human myelomonocyte IFN-gamma on HuIFN-gamma susceptible diseases

Experiment 3-1

Virus inhibitory activity in vitro

A primary monolayer culture of human fetal lung in a 6 cm Petri dish was combined with a human myelomonocyte IFN-gamma prepared by the method of Example B-1(3) in an inoculum of 0.1, 1.0 or 10.0 units. This culture was incubated in 5% $CO_2$ incubator at 37° C. for 20 hours. To the resultant culture was added either varicella-zoster virus or human cytomegalovirus in a dose that was capable of forming 100 plaques in the absence of human myelomonocyte IFN-gamma.

The virus inhibitory activity was determined with the decreasing rate of the plaque number.

$$\text{Plaque reduction rate } (\%) = \frac{A - B}{A} \times 100$$

wherein A designates the plaque number with no addition of human myelomonocyte IFN-gamma; B is the plaque number with addition human myelomonocyte IFN-gamma.

The results are shown in Table V.

TABLE V

| Human myelomonocyte IFN-gamma (units) | Varicella-zoster virus | Cytomegalovirus |
|---|---|---|
| 0.1 | 11% | 10% |
| 1.0 | 54% | 49% |
| 10.0 | 93% | 88% |

These results confirmed that the human myelomonocyte IFN-gamma used in the invention was very effective in inhibiting the growth of pathogenic viruses.

Experiment 3-2

Treatment of malignant tumors with human myelomonocyte IFN-gamma

Experiment 3-2(1)

Cytostatic activity of human myelomonocyte IFN-gamma on malignant tumors in vitro An aliquot of RPMI 1640 medium supplemented with 15 v/v% of fetal calf serum was added to a human myelomonocyte IFN-gamma prepared by the method of Example B-1(3) to a final concentration of 5, 50 to 500 units/ml, and the mixture was inoculated with a malignant human tumor cell to $5 \times 10^5$ cells/ml. The resultant mixture was incubated in a 5% $CO_2$ incubator at 37° C. for three days. As a control, the same amount of a human myelomonocyte IFN-gamma preinactivated by 30 minutes of incubation at 100° C. was added to a fresh preparation of the same culture medium and the mixture was treated as above. After culturing, the viable cells were stained with neutral red in accordance with the method described in *Applied MIcrobiology*, Vol, 22, No. 4, pp. 671–677 (1977). Thereafter, the neutral red was eluted with acidified ethanol, and the number of viable cells was determined with absorbance of the eluate at 540 nm.

The cytostatic rate (%) was determined by using the following equation:

$$\text{Cytostatic rate (\%)} = \left(1 - \frac{A}{B}\right) \times 100$$

wherein A is the number of viable cells in the test system, and B is the number of viable cells in the control.

The results are shown in Table VI

TABLE VI

| Human myelomonocyte IFN-gamma (Unit/ml) | Tumor cell | | | |
|---|---|---|---|---|
| | KB | HEp-2 | KATO-II | P-4788 |
| 5 | 18% | 14% | 28% | 9% |
| 50 | 72% | 31% | 60% | 22% |
| 500 | 93% | 53% | 85% | 43% |

Note: KB cell is of human oral epidermoid carcinoma origin; HEp-2 cells of human larynx epidermoid carcinoma origin; KATO-II cells, human stomach carcinoma origin; P-4788, human colon carcinoma origin.

These results confirmed that the human myelomonocyte IFN-gamma of the present invention when used at a concentration of 5–500 units/ml strongly inhibited the growth of malignant tumor cells such as KB cells, HEp-2 cells, KATO-II cells, and P-4788 cells.

Experiment 3-2(2)

Potentialization of cytostatic activity of other lymphokines by human myelomonocyte IFN-gamma in vitro The lymphokines used in this experiment were human myelomonocyte IFN-gamma (5 units/ml), HuIFN-alpha (50 units/ml) and TNF (10 units/ml). The HuIFN-alpha and TNF were natural products derived from lymphoblastoid cells.

These lymphokines were tested for cytostatic rate (%) in accordance with the method of Experiment 3-2(1). The results are shown in Table VII.

TABLE VII

| Human myelomonocyte IFN-gamma (Unit/ml) | Tumor cell | | | |
|---|---|---|---|---|
| | KB | HEp-2 | KATO-II | P-4788 |
| Human mylemonocyte INF-gamma | 16% | 14% | 26% | 9% |
| HuIFN-alpha | 9% | 6% | 11% | 5% |
| TNF | 5% | 6% | 10% | 6% |
| Human mylemonocyte INF-gamma plus HuIFN-alpha | 45% | 30% | 43% | 27% |
| Human mylemonocyte INF-gamma plus TNF | 70% | 51% | 54% | 42% |
| Human mylemonocyte INF-gamma, HuIFN- plus TNF | 92% | 65% | 78% | 61% |

These results confirmed that human myelomonocyte IFN-gamma greatly enhanced the cytostatic effect of other lymphokines on malignant tumors and that the enhancement was synergistic.

Experiment 3-2(3)

Potentialization of cytostatic activity of chemotherapeutics on malignant tumors by human myelomonocyte IFN-gamma in vitro One ml aliquots of a nutrient culture medium prepared in accordance with the method of Experiment 3-2(1) were inoculated with $10^6$ cells of a human malignant tumor cell, and the mixture was cultured for one day. To the resultant culture was added 50 units of a human myeloncyte IFN-gamma prepared by the method of Example B-1(3) and/or 0.1 ml saline containing a chemotherapeutic, and cultured at 37° C. for two days. As a control, a saline solution free of human myelomonocyte IFN-gamma and chemotherapeutic was used. After culturing, the cytostatic rate (%) was determined in accordance with the method of Experiment 3-2(1). The concentrations of the chemotherapeutics used were as follows: nimustin hydrochloride (ACNU), $1.0 \times 10^{-6}$ g/ml; fluorouracil (5-FU), $1.5 \times 10^{-8}$ g/ml; doxorubicin (ADM), $1.0 \times 10^{-10}$ g/ml; mitomycin C (MMC), $2.5 \times 10^{-9}$ g/ml; and vincristin sulfate (VCR), $1.5 \times 10^{-10}$ g/ml.

The results are shown in Table VIII

TABLE VIII

| Chemo-therapeutic | Human myelomonocyte IFN-gamma | Tumor cell | | | |
|---|---|---|---|---|---|
| | | HEp-2 | PC-9 | HLE | HeLa |
| — | − | 38% | 53% | 44% | 52% |
| ACNU | − | 4% | 2% | 5% | 5% |
| | + | 54% | 65% | 63% | 72% |
| 5-FU | − | 8% | 10% | 8% | 12% |
| | + | 67% | 68% | 71% | 70% |
| ADM | − | 13% | 6% | 7% | 17% |
| | + | 59% | 72% | 62% | 64% |
| MMC | − | 10% | 5% | 12% | 7% |
| | + | 61% | 64% | 65% | 62% |
| VCR | − | 5% | 8% | 10% | 10% |
| | + | 58% | 66% | 58% | 65% |

Note: (−) means with no addition; and (+) with addition. HEp-2 cell is of human larynx epidermoid carcinoma origin; PC-9, of human lung carcinoma origin; HLE, of human liver carcinoma; and HeLa, of human cervix epitheloid carcinoma origin.

The above results confirmed that human myelomonocyte IFN-gamma greatly enhanced the cytostatic activity of chemotherapeutics on malignant tumors. The enhancement was arithmetic or synergistic.

Experiment 3-2(4)

Cytostatic activity on malignant tumors in vivo

BALB/c nude mice were implanted at the dorsal area with a segment of human breast cancer tissue. From the time the tumors reached about 200 nm$^3$, the nude mice were injected once every day with one or more human myelomonocyte IFN-gamma prepared by the method of Example B-1(3), a lymphokine derived from human lymphoblastoid cell, and/or a chemotherapeutic in saline solution over a period of 20 days.

Thereafter, the nude mice were sacrificed, and the tumors were weighed.

As a control, saline solution was injected as above.

These results confirmed that human myelomonocyte IFN-gamma greatly inhibited the growth of malignant tumors in vivo. The cytostatic activity was greatly enhanced to exert a strong antioncotic effect by combining one or more lymphokines or chemotherapeutics with the human myelomonocyte IFN-gamma.

TABLE IX

| Treatment | Dose/kg/day | Tumor (g) |
|---|---|---|
| Control | — | 10.8 ± 1.0 |
| Human myelomonocyte IFN-gamma | 50 units | 6.5 ± 0.9* |
| HuIFN-alpha | 500 units | 7.1 ± 0.8* |
| TNF | 100 units | 6.4 ± 0.5* |
| MMC | 1 mg | 5.1 ± 0.4* |
| Human myelomonocyte IFN-gamma plus HuIFN-alpha | 500 units / 100 units | 4.6 ± 0.5* |
| Human myelomonocyte IFN-gamma plus TNF | 50 units / 100 units | 4.3 ± 0.5* |
| Human myelomonocyte IFN-gamma plus MMC | 50 units / 1 mg | 3.9 ± 0.4* |
| Human myelomonocyte IFN-gamma HuIFN-alpha plus TNF | 50 units / 500 units / 100 units | 2.7 ± 0.5* |
| Human myelomonocyte IFN-gamma Hu-IFN alpha plus MMC | 50 units / 500 units / 1 mg | 2.6 ± 0.6* |

Note: The values were stochastically significant against the control at a significance level of 5%.

Experiment 3-2(5)

Acute toxicity

The acute toxicity of a human myelomonocyte IFN-gamma preparation obtained by the method of Example B-1(3) was tested using 20-day old mice.

The result of this testing confirmed that the toxicity of the human myelomonocyte IFN-gamma was extremely low, i.e., on the order of 10$^9$ units or more as expressed as LD$^{50}$ when injected intraperitoneally.

The following examples illustrate preparing pharmaceutical compositions containing human myelomonocyte IFN-gamma prepared according to the present invention as an active ingredient.

Example C-1

Liquid medicine

A liquid medicine was prepared by dissolving in saline a human myelomonocyte IFN-gamma obtained by the example of Example B-1(3) at a concentration of 500 units/ml.

The products can be used in the form of nebula, collyrium, collunarium or colutorium for prophylactic and therapeutic agents for viral diseases such as epidemic conjunctivitis and influenza.

Example C-2

Injection

AS solid injection was obtained by dissolving in saline 100,000 units/ml of a human myelomonocyte IFN-gamma obtained by the example of Example B-2(3). The solution was filtered under sterile conditions, 2 ml aliquots of the filtrate were distributed to vials an lyophilized. The vials were then sealed. This product is useful as a prophylactic and therapeutic agent for viral diseases as the product of Example C-1.

The product is also suitable for prophylactic and therapeutic agent for malignant tumors such as breast cancer, lung carcinoma, liver carcinoma ad leukemia, as well as immunopathies such as atopic allergy, pernicious anemia, articular rheumatism and systemic lupus erythematosus.

The products is suitable as an enhancer for chemotherapeutics such as melphalan, methotrexate and ADM.

Example C-3

Injection

Ten thousand units/ml of a human myelomonocyte IFN-gamma prepared by the method of Example B-3, 100,000 units.ml of natural lymphoblastoid HuIFN-alpha, and 100,000 units/ml of natural lymphoblastoid TNF were added to saline. The mixture was filtered under sterile conditions and lyophilized as in Example C-2 to yield a solid injection.

The product is suitable for prophylactic and therapeutic agents for viral diseases. The product is also suitable for use as a prophylactic and therapeutic agent for malignant tumors such as breast cancer, lung carcinoma, liver carcinoma, stomach cancer and leukemia; as well as immunopathies such as atopic allergy, collagenasis, articular rheumatism, and systemic lupus erythematosus.

The product can be used to enhance the cytostatic activity of chemotherapeutics such as tegafur, MMC and VCR.

Example C-4

Ointment

A human myelomonocyte IFN-gamma prepared by the method of Example B-1(3) and a natural lymphoblastoid HuIFN-alpha were kneaded together with a small amount of liquid paraffin in a conventional manner, and the mixture was added to white petrolatum to yield concentrations of human myelomonocyte IFN-gamma and HuIFN-alpha of 50,000 units/g and 500,000 units/g, respectively.

The product is suitable for prophylactic and therapeutic use for treating skin diseases such as herpes, skin carcinoma, and atopic dermatitis.

Example C-5

Enteric coated tablet

A human myelomonocyte IFN-gamma prepared by the method of Example B-5 and a natural lymphoblastoid TNF were incorporated into a conventional tablet using starch and maltose as vehicles. The active ingredients were present in the amounts of 10,000 units per tablet each, each tablet weight 200 mg. The tablets were then coated with methylcellulose phthalate.

The product is useful for prophylactic and therapeutic treatment of viral diseases such as those in the small and large intestines, as well as for malignant tumors such as colon carcinoma and liver carcinoma, and immunopathies such as atopic allergy, pernicious anemia, articular rheumatism, and systemic lupus erythematosus.

The product can be used to enhance the antioncotic activity of chemotherapeutics such as ADM, 5-FU and MMC.

As described above, conventional processes provide insufficient amounts of HuIFN-gamma to be useful in preparing HuIFN-gamma on an industrial scale. Although it is recognized that conventional human myelomonocytes provide a superior HuIFN-gamma and produce a novel HuIFN-gamma, the present invention provide a novel human myelomonocyte IFN-gamma and a process for preparing this IFN-gamma which is capable of being prepared on an industrial scale.

The present invention also provides a process for preparing a monoclonal antibody using the human myelomonocyte IFN-gamma thus obtained, as well as providing a purification method using the antibody. The present invention also provides prophylactic and therapeutic agents for treating HuIFN-gamma susceptible diseases. The agent is very effective in treating viral disease, malignant tumors, rheumatism and immunopathies, treatment of which heretofore has been very difficult.

The present invention is a significant contribution to the art.

We claim:

1. A prophylactic and therapeutic composition for human interferon-gamma-susceptible diseases comprising an effective amount of human myelomonocyte interferon-gamma for preventing or treating said human interferon-gamma-susceptible diseases and a pharmaceutically acceptable carrier.

2. The composition of claim 1 wherein said human myelomonocyte interferon-gamma is produced by:
propagating an established human myelomonocyte which produces myelomonocyte interferon-gamma and
recovering and purifying the interferon-gamma produced by said myelomonocyte.

3. The composition of claim 2 wherein said established human myelomonocyte is produced by:
implanting an established human myelomonocyte capable of producing human myelomonocyte interferon-gamma in a non-human warm-blooded animal; and
allowing said established human myelomonocyte to proliferate while allowing said established human myelomonocyte to contact blood, ascites, or urine from the non-human warm-blooded animal in order to supply the nutrients in the blood, ascites or urine to the established human myelomonocyte.

4. The composition of claim 2 wherein said established human myelomonocyte is selected from the group consisting of HBL-38 cells, HL-60 cells (ATCC CCL 240), KG-1 cells (ATCC CCL 246). ML-1 cells, ML-2 cells, ML-3 cells, THP-1 cells (ATCC TIB 202), U-937 cells (ATCC CRL 1593) and CTV-1 cells.

5. The composition of claim 2 wherein said human myelomonocyte interferon-gamma is purified by column chromatography using an anti-interferon-gamma antibody.

6. The composition of claim 2 wherein said established human myelomonocyte is contacted with an inducer.

7. The composition of claim 1 wherein said inducer is selected from the group consisting of phytohemagglutinin, concanavalin A, pokeweed mitogen, lipopolysaccharide, lipid A, endotoxin, polysaccharide, bacteria, antigens, and mixtures thereof.

8. The composition of claim 1 wherein said composition is used as an antiviral agent, an antioncotic, an enhancer for antioncotic, a depressant for metastasis of a malignant tumor, an immunoregulator, a therapeutic composition for rheumatism, or a therapeutic agent for immunopathy.

9. The composition of claim 1 in which said human myelomonocyte interferon-gamma is present in the range of 1-10,000 units/g.

10. The composition of claim 1 which further contains a lymphokine.

11. The composition of claim 1 wherein said lymphokine is selected from the group consisting of interferon-alpha, interferon-beta, tumor necrosis factor, lymphotoxin, interleukin 2, B-cell differentiating factor, and mixtures thereof.

12. A human myelomonocyte interferon-gamma.

13. The human myelomonocyte interferon-gamma of claim 12 which is obtained by:
propagating an established human myelomonocyte which produces myelomonocyte interferon-gamma; and
recovering and purifying the interferon-gamma produced by said myelomonocyte.

14. The human myelomonocyte interferon-gamma of claim 13, wherein said established human myelomonocyte is obtained by:
implanting an established human myelomonocyte capable of producing human myelomonocyte interferon-gamma in a non-human warm-blooded animal or inoculating the established human myelomonocyte capable of producing human myelomonocyte interferon-gamma into a diffusion chamber placed inside or outside the body of a non-human warm-blooded animal; and allowing the established human myelomonocyte to proliferate while allowing the established human myelomonocyte to contact the blood, ascites, or urine from the non-human warm-blooded animal in order to supply nutrients from the blood, ascites, or urine from the non-human mammal to the established human myelomonocyte.

15. The human myelomonocyte interferon-gamma of claim 13 wherein said established human myelomonocyte is selected from the group consisting of HBL-38 cells, HL-60 cells (ATCC CCL 240), KG-1 cells (ATCC CCL 246), ML-1 cells, ML-2 cells, ML-3 cells, THP-1 cells (ATCC TIB 202), U-937 cells (ATCC CRL 1593) and CTV-1 cells.

16. The human myelomonocyte interferon-gamma of claim 13 wherein said interferon-gamma is purified by column chromatography using an anti-interferon-gamma antibody.

17. The human myelomonocyte interferon-gamma of claim 13, wherein said established human myelomonocyte is contacted with an inducer.

18. The human myelomonocyte interferon-gamma of claim 17 wherein said inducer is selected from the group consisting of phytohemagglutinin, concanavalin A, pokeweed mitogen, lipopolysaccharide, lipid A, endotoxin, polysaccharide, bacteria, antigens, and mixtures thereof.

19. A method for treating diseases which are susceptible to treatment by human myelomonocyte interferon-gamma comprising administering to a patient suffering from a disease which is susceptible to treatment by human myelomonocyte interferon-gamma an effective amount to treat said disease which is susceptible to such treatment of a composition according to claim 1.

20. The method according to claim 19 wherein said disease is selected from the group consisting of viral diseases, malignant tumors, leukemia, atopic allergy, pernicious anemia, articular rheumatism and systemic lupus erythematosus.

21. The method according to claim 19 wherein said composition further includes a lymphokine.

22. The method according to claim 21 wherein said lymphokine is selected from the group consisting of interferon-alpha, interferon-beta, tumor necrosis factor, lymphotoxin, interleukin 2, B cell differentiating factor, and mixtures thereof.

* * * * *